United States Patent [19]

Koehn

[11] 3,943,225
[45] Mar. 9, 1976

[54] CATHETER
[75] Inventor: Wilbur R. Koehn, Sands Point, N.Y.
[73] Assignee: ProMed Laboratories Inc., Huntington Station, N.Y.
[22] Filed: Dec. 3, 1973
[21] Appl. No.: 420,881

Related U.S. Application Data
[63] Continuation of Ser. No. 148,103, May 28, 1971, abandoned.

[52] U.S. Cl. ............... 264/255; 128/214.4; 264/25; 264/259; 264/264; 264/294; 264/310; 264/323
[51] Int. Cl.² ..................... B29C 13/00; B29D 9/00
[58] Field of Search ............ 264/25, 310, 259, 271, 264/279, 299, 323, 264, 294; 117/94; 128/214.4, 221; 118/44, 404

[56] References Cited
UNITED STATES PATENTS

| | | | |
|---|---|---|---|
| 2,305,005 | 12/1942 | Henry | 118/404 |
| 2,647,296 | 8/1953 | Shive | 118/44 X |
| 2,786,252 | 3/1957 | Curran | 264/271 X |

Primary Examiner—Robert F. White
Assistant Examiner—Thomas P. Pavelko
Attorney, Agent, or Firm—Curtis, Morris & Safford

[57] ABSTRACT

A method and apparatus is disclosed for making a combined needle and catheter of the type in which the needle is used to lead the end of the catheter thereon into a body cavity and, after insertion, is withdrawn through the catheter with most of the catheter remaining in the body. To form the catheter, the needle is initially placed in an upright position with its pointed end downward and located within the orifice of a die wiper. Thereafter, a measured quantity of a viscous plastic material or fluid plastisol is applied to the die wiper on the side thereof opposite the pointed end of the needle and the assembly of needle, die wiper and plastisol is then inverted so that the die wiper falls by gravity and wipes a coating of fluid plastisol along the shank of the needle. When the die wiper has completed its traverse of the needle shank, the assembly is heated to solidify the fluid plastisol on the needle and thereby form a removable flexible catheter on the needle.

25 Claims, 19 Drawing Figures

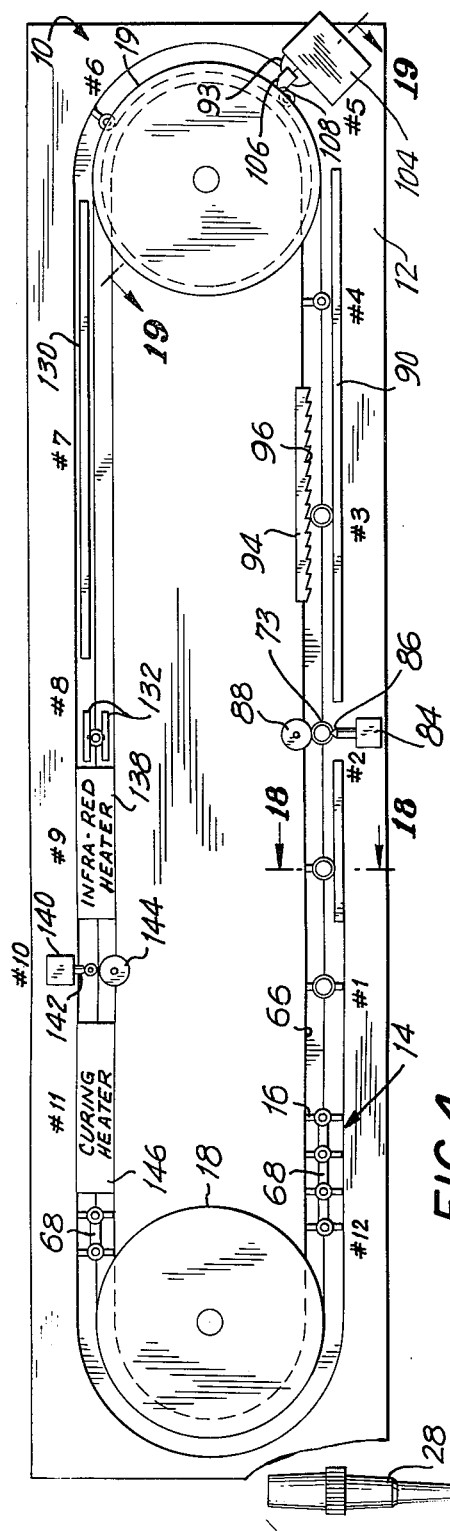
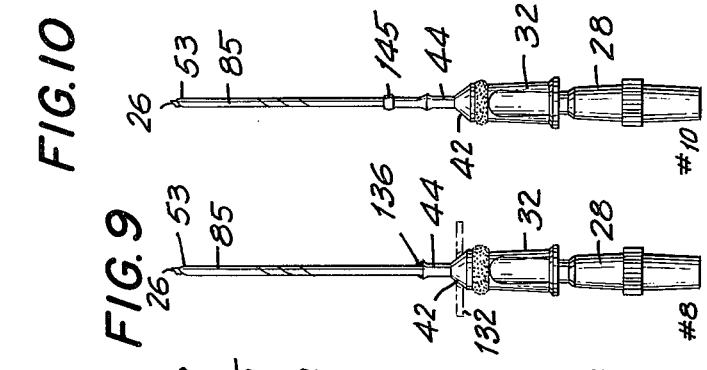
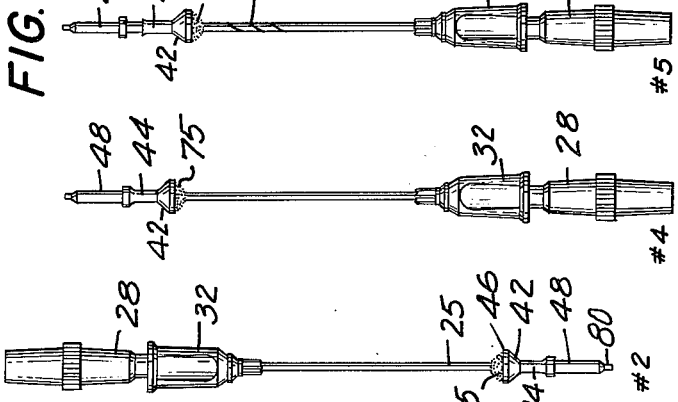
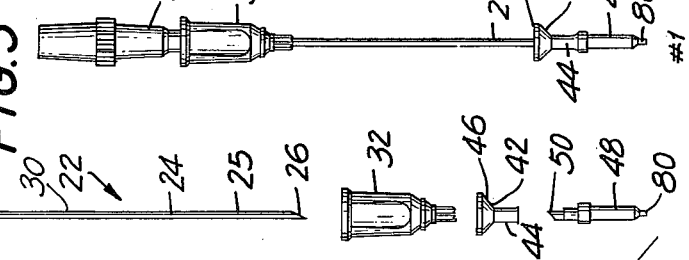

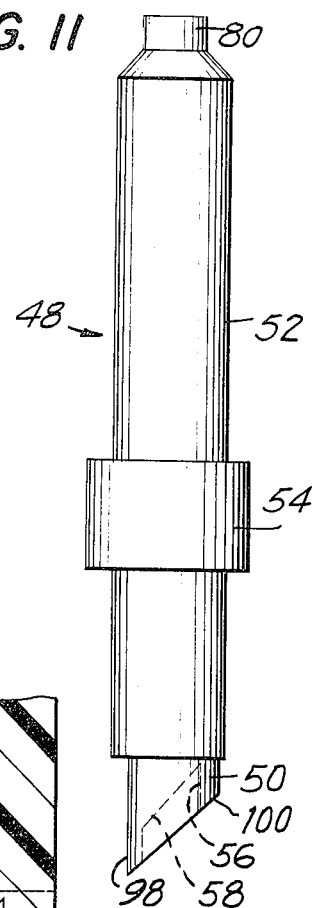
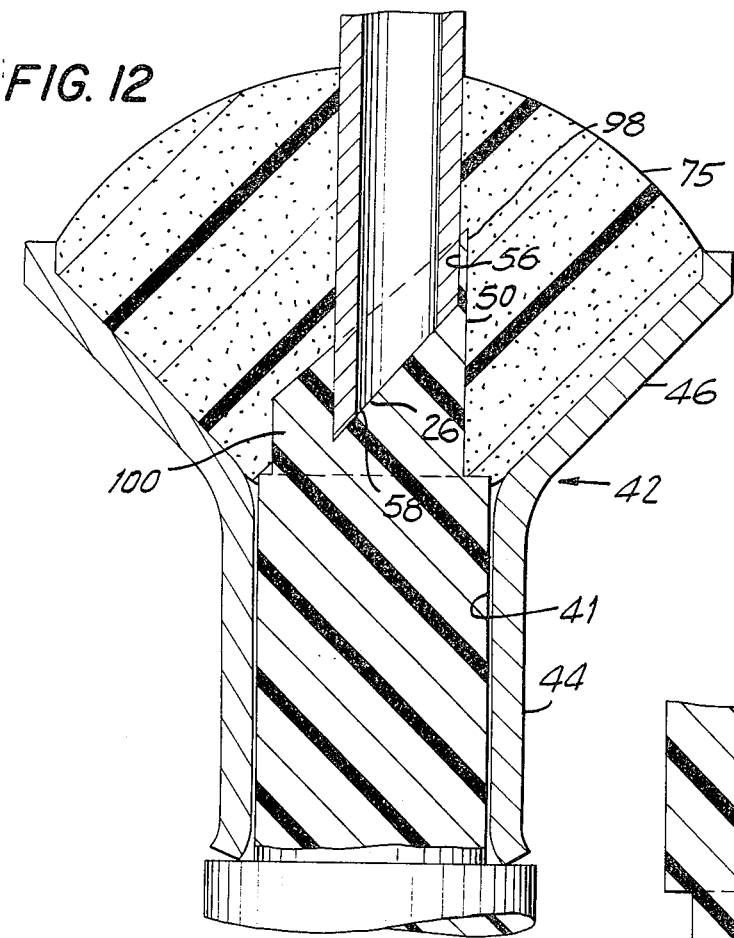
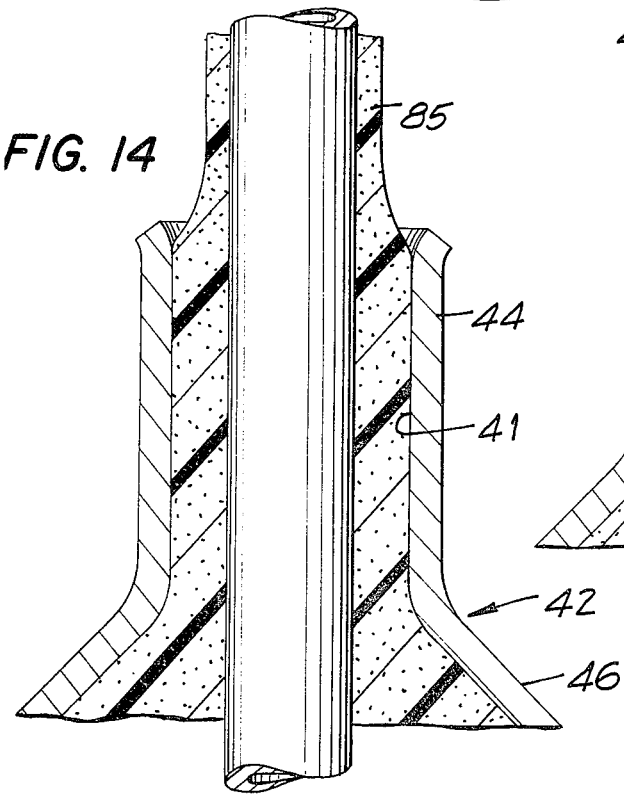
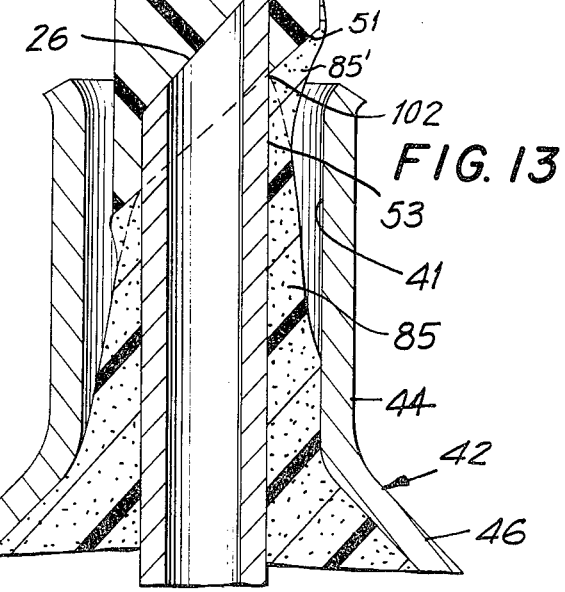

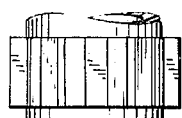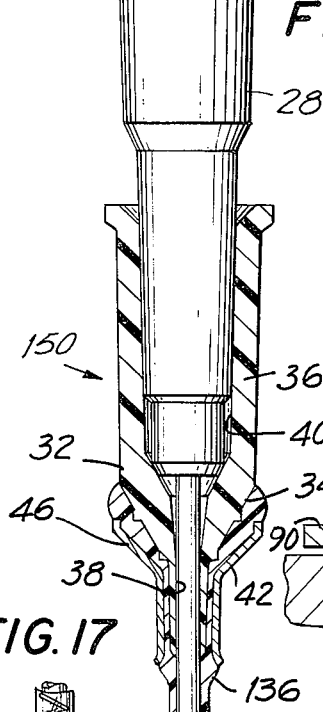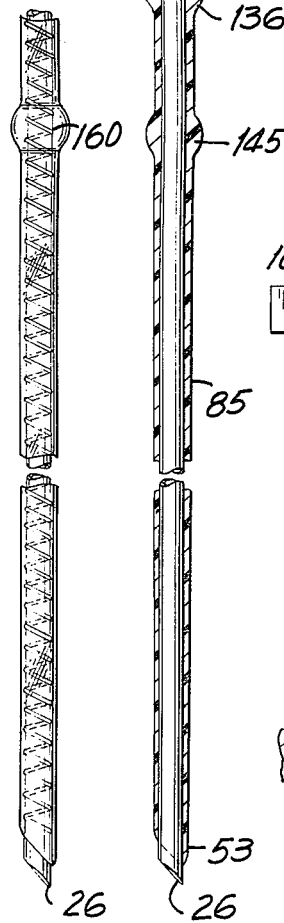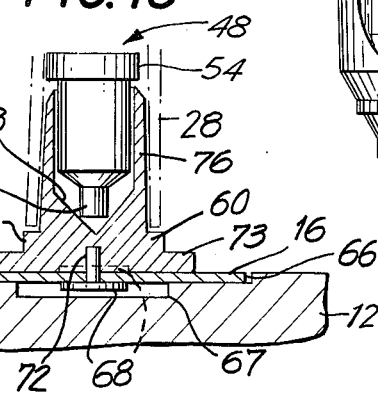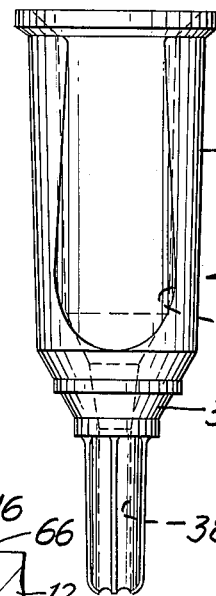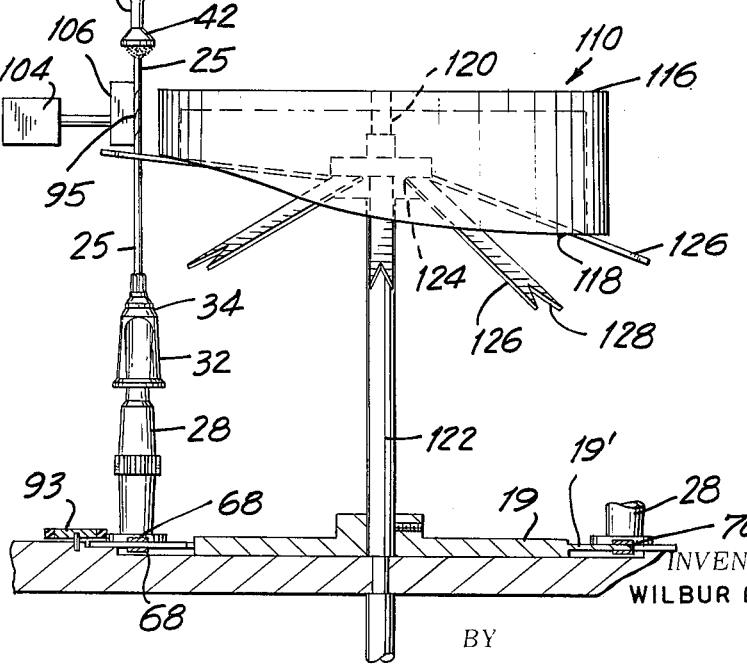

CATHETER

This is a continuation, of application Ser. No. 148,103, filed May 28, 1971 now abandoned.

The present invention relates to surgical catheters and more particularly to a method and apparatus for fabricating a catheter directly on a needle and the resulting combined needle and catheter which facilitates insertion of the catheter into a bodycavity.

One previously proposed surgical catheter of the above type is described in my prior U.S. Pat. No. 3,204,634, which described and claims a combined needle and catheter that permits the forward end of the catheter to follow the pointed end of a needle into a body cavity or vein. After the end of the catheter has entered the body cavity the rearward end of the catheter is held by one hand and the needle withdrawn through the catheter with the other hand. The catheter described in my prior patent is made by dipping a needle into a supply of liquid plastisol to a point just below the pointed end of the needle to coat the shank thereof with the plastisol. The coated needle is then removed and held by its pointed end so that the plastisol will drain downwardly on the needle and form a uniform coating with a tapered portion adjacent the pointed end of the needle. The combined needle and catheter made by this method has been tested extensively and found to be quite satisfactory in use.

Other methods have previously been proposed for making a combined needle and catheter in which a plastic tube is provided around a needle. Typically, such methods involve the use of extruded tubing which is separately formed, cut and then placed on the needle. Such methods have not been entirely satisfactory for numerous reasons. For example, the catheter must be provided with a fitting at its rearward end which provides a detachable connection to a syringe or extension tube through which fluids may be supplied or withdrawn through the catheter. Since the catheter and fitting are formed in separate pieces and subsequently joined together, typically by means of an adhesive which secures the catheter tube shank to its fitting, the point of joinder therebetween represents a weak point in the assembly and as a result, bending stresses applied to that point during movement of the patient's arm may cause the catheter shank in break off or separate from its fitting. Also, the extruded tubes used to form such catheters are formed of relatively stiff materials and tend to crack or break under stress. As a result, with such previously proposed catheters, the entire catheter shank or a portion thereof may break off and pass through the circulation system to the heart or lung of the patient, causing serious damage and trauma to him and requiring intricate surgical procedures to remove the catheter from the body of the patient. This hazard has inhibited the routine use of previously proposed catheters in spite of the many benefits of using relatively flexible plastic tube in lieu of a rigid metal needle.

Another disadvantage of the combined needles and catheters previously proposed is that the leading edge of the catheter is apt to be too blunt and forms an annular shoulder about the needle shank which is not only difficult to pass through the skin but often results in the catheter "curling back" over the needle during insertion. Even if the leading edge of the plastic tube is beveled, to correspond to the beveled pointed tip of the needle, a shoulder is still formed about the leading edge of the tube which hinders insertion thereof. No previously proposed combined needle and catheter, other than that disclosed in my above-identified patent, has been produced in which the leading edge of the catheter has a combined feathered and beveled edge to provide a smooth tapered increase in diameter from the shank of a bevel-edged needle to the outside diameter of the catheter to facilitate insertion.

Accordingly, it is an object of the present invention to provide an improved method of fabricating a catheter directly on a needle used to insert the end of the catheter in a body cavity.

It is another object of the present invention to provide a combined catheter and needle assembly wherein the catheter has a feathered leading edge and a tapered shank portion to facilitate insertion of the combined catheter and needle through the skin.

Still another object of the present invention is to provide a flexible catheter having means integral therewith for limiting the length of the catheter which may be inserted into a body cavity.

Still another object of the invention is to provide an improved catheter and needle unit which is of relatively simple and compact construction, adapted for economical manufacture as a disposable unit and one which is reliable in operation for inserting the end of a plastic catheter into a body cavity.

In accordance with an aspect of the present invention an improved method of forming a combined needle and catheter, similar to that described and claimed in my above-mentioned patent, is provided wherein the shank of a needle having an enlarged hub or handle at one end and a beveled cutting edge at its opposite end for leading the end of a catheter thereon into a body cavity is used as a mandrel for forming the catheter directly on the needle. The needle is initially inserted through a hollow preformed plastic fitting and the exterior surface of the needle handle is frictionally engaged with the interior of the fitting. The needle is then inserted through the central orifice of a die wiper having a cup-shaped reservoir portion opening towards the catheter fitting member and the penetrating end of the needle is thereafter inserted in a guide member which is adapted to support the entire assembly in a first position. The guide member has a beveled end portion which receives and closely fits the beveled end of the needle and a surrounding shoulder which defines the leading edge of the catheter to be formed on the needle.

The entire assembly of needle, catheter fitting, die wiper and guide member is placed in an upright position on a continuous conveyor at the first station of the apparatus of the present invention with the guide member at the lower end of the assembly and the upper portion of the guide member surrounded by said die wiper. The assembly is moved in this configuration through the next station of the apparatus where a measured quantity of viscous plastic material or fluid plastisol of a plastic resin is placed in the cup-shaped reservoir of the die wiper about the needle and the upper portion of the guide. During application of the plastisol to the die wiper the entire assembly is rotated about its central vertical axis to fully distribute the plastisol in the reservoir and wet the needle. Thereafter, the assembly is inverted so that the die wiper falls by gravity and wipes a uniform wall of fluid plastisol along the shank of the needle.

An inert radio opaque material is applied to a predetermined portion of the needle prior to passage of the die wiper and plastisol thereover. This material is applied in the remote event that the forward portion of the catheter does break off and enters a vein or other body cavity so that such portion may be found by X-ray examination and immediately removed by the appropriate surgical procedures.

After the wiper has wiped a coating of plastisol in the entire shank of the needle and onto the upper end of the catheter fitting, the assembly is moved through a heater which unites the fluid plastisol coating with the end of the fitting and cures and solidifies the plastisol coating on the needle to form a removeable flexible catheter thereon. Thereafter, an annular bead of liquid plastisol is applied to a predetermined portion of the catheter and when heated (solidified) thus forms a safety stop member on the catheter adjacent the fitting.

The initial heating of the catheter securely unites the coated catheter shank to the catheter fitting into a one-piece integral structure; as a result of the heating the die wiper is secured to the catheter and serves as a reinforcement at the point of joinder between the shank and fitting thereof. The bead of plastisol serves as a stop member when the needle and catheter is inserted into the body and limits movement of the assembly into the body to a predetermined depth. Further, in the event that the catheter should separate from its fitting at the point of junction therebetween, the bead would prevent the catheter from slipping through the skin into the body.

The above, and other objects, features and advantages of this invention, will be apparent in the following detailed description of illustrative embodiments thereof which is to be read in connection with the accompanying drawings, wherein:

FIG. 1 is a plan view of a preferred embodiment of an apparatus for producing combined needles and catheters in accordance with the method of the present invention;

FIG. 2 is an exploded view of the elements used to form the combined needle and catheter in the apparatus illustrated in FIG. 1;

FIGS. 3–10 illustrate the configuration of the components of FIG. 2 at selected stations in the apparatus of FIG. 1;

FIG. 11 is an enlarged view of the guide member into which the penetrating tip of the needle is inserted and supported;

FIG. 12 is an enlarged sectional view of the needle guide, die wiper and plastisol at the stage of the process illustrated in FIG. 4;

FIG. 13 is a view similar to FIG. 12, illustrating the relative configuration of the various components at the stage of the process illustrated in FIG. 6;

FIG. 14 is a view similar to FIG. 12 and illustrates the relative configuration of the die wiper, needle and plastisol during the stage of the process illustrated in FIG. 8;

FIG. 15 is an enlarged view of one embodiment of the part forming the catheter fitting;

FIG. 16 is an enlarged view partly in section, illustrating the completed combined needle and catheter assembly;

FIG. 17 is a view, partly in section, of a combined needle and cather of modified construction having a reinforced catheter wall;

FIG. 18 is a sectional view taken on line 18—18 of FIG. 1; and

FIG. 19 is an elevational view partly in section taken at line 19—19 of FIG. 1 to show the structure for applying a spiral marking of radio opaque material on the shank of the needle.

Referring to the drawings in detail, and initially to FIG. 1 thereof, it will be seen that the preferred apparatus 10, as shown therein, for performing the process of the present invention has a work surface 12 which supports a horizontally extending conveyor system 14. The latter is adapted to move an assembly of catheter and needle components throgh a plurality of operating stations legended 1–12, respectively, in the drawing.

Conveyor system 14, although not shown in detail, includes a chain of connected links 16 movable in a suitable track on the surface 12 and around a pair of end pulleys 18 and 19, the former being driven by an electric motor or the like (not shown) to move the conveyor through the apparatus at a predetermined constant speed.

The assembly of parts utilized to form the combined needle and catheter of the present invention is illustrated in FIG. 2 and is indicated generally by the reference character 20. Assembly 20 includes a mandrel 22 which, in the preferred embodiment of the present invention, comprises the shank 25 of a steel needle 24 having a beveled penetrating end 26 and a handle 28 secured to the opposite or rearward end 30 of needle shank 25. Tip 26 and shank 25 are inserted through a preformed plastic member 32 which forms the catheter fitting in the completed combined needle and catheter assembly.

The part 32 is constructed of a suitable plastic resin, of the same kind as the remainder of the catheter to be formed, and as illustrated in detail in FIG. 15 includes a generally conical shaped neck 34 and an enlarged socket 36. Neck 34 includes an internal bore 38, having a diameter substantially equal to the outside diameter of needle shank 25 and through which the needle shank is inserted in the completed assembly. Base 36 includes an enlarged bore section 40 for surrounding and receiving handle 28 of the needle. When the needle is inserted through part 32 its handle 28 is moved into frictional engagement with socket 36 which is a Luer-type, standard surgical fitting. The exterior surface of needle handle 28 corresponds to the male portion of this type fitting and, thus, the two hubs are frictionally maintained in engagement.

After insertion of needle shank 25 through part 32, needle point 26 and shank 25 are inserted through the central orifice 41 of a die wiper 42. This die wiper (FIG. 12) has a larger diameter than the outside diameter of needle shank 25 so that the needle may pass freely therethrough. The die wiper includes an elongated neck section 44 and a conical, cup-shaped reservoir section 46 and is positioned on needle 24 with reservoir 46 opening towards the catheter fitting 32 and needle handle 28, for reasons more fully described hereinafter.

The final member of assembly 20 is a guide 48 having a recessed tip 50 which is adapted to receive the beveled penetrating end 26 of needle 25. Guide 48 is more clearly illustrated in FIG. 11 wherein it is seen that the guide comprises a generally cylindrical main portion 52 having an enlarged cylindrical shoulder portion 54. Tip 50 has a cylindrical recess 56 therein which receives the tip 26 of needle 24 with a close fit. The bottom half 58 of recess 56 is inclined at an angle corresponding to the beveled end 26 of the needle tip 26 so that when the needle tip is inserted in recess 56 its beveled end will tend to be cammed into alignment with the beveled bottom wall 58 on which it seats to securely support needle 24 in the guide. Recess 56 is symmetrical about the center line of the main portion 52 of the bevel guide. However, tip 50 is slightly offset fro the center line for reasons more fully explained hereinafter.

When all components of assembly 20 are put together in the manner described above, they are in the configuration illustrated in FIG. 3 and mounted in apparatus 10 at station 1, that is, with the die wiper 42 resting at the lower end of the assembly on guide 48. The assembly is supported by the bevel guide 48 on a base structure 60 rotatably mounted on a chain link 16. The latter, as shown in FIG. 18, rides in a first slotted track 66 on work surface 12. Links 16 are pivotally interconnected by pairs of links 68 that give the chain flexibility and which define a space 70 therebetween (FIG. 19) in which the teeth 19' of sprockets 18 and 19 are engaged to drive chain 14 about the apparatus. The lower link of the pair 68 is accommodated in a second slot 67 in work surface 12.

Member 60 is rotatably mounted on a pin 72 extending from link 16 and may be removable therefrom so that the number and spacing of mounting members on chain 16 may be selected as desired. Mounting member 60 includes a flat disk-shaped base member 73 and a first cylindrical boss 74 concentric with its axis of rotation, the outside diameter of which corresponds to the inside diameter of the hollow needle handle 28. A second concentric cylindrical extension 76 is also provided which has a recess 78, the diameter of which corresponds to the diameter of the main portion 52 of bevel guide 48. At station 1 portion 52 of guide 48 is inserted in recess 78 (as shown in FIG. 18) to support the entire assembly on the apparatus for transportation therethrough by conveyor system 14.

After assembly 20 is placed on mounting member 60 at station 1, conveyor 14 transports the assembly to station 2, (see FIG. 1) where a supply of viscous or semi-viscous material or liquid plastisol 75 is applied to reservoir 46 of die wiper 42. It is noted that while the illustrative embodimemnt of the present invention is described in relation to a fluid plastisol, other mentioned materials, i.e. viscous or semi-viscous plastic materials which are well known may also be used.

Plastisol 75 may be composed of any suitable resin like those described in my prior U.S. Pat. No. 3,204,634, referred to above, the appropriate portion of which is hereby incorporated by reference. The plastiosol is supplied by an impulse pump 84 through a nozzle 86 positioned slightly above the level of die wiper 42. A microswitch (not shown) is positioned adjacent track 66 and is engaged by a portion of assembly 20, e.g. member 48, as it arrives at station 2 to energize pump 84. A drive wheel 88 is also located at station 2 and is driven by a motor (not shown). Wheel 88 contacts base 73 of mounting member 60 as the latter is conveyed forwardly and rotates the mounting member and thus the entire assembly as it passes through station 2 so that the supply of liquid plastisol is distributed substantially uniformly about the annular extent of reservoir 46. This step occurs as the assembly is moving through station 2 and in the preferred embodiment chain 16 is moved continuously through the station.

A rail 90 extends along the path of travel of chain 16 between station 1 and station 4 as illustrated in FIG. 1 and has an elastic surface portion 92 (FIG. 18) which engages base 73 of mounting member 60 as it travels along the length thereof. The frictional engagement of base 73 along with the movement of assembly 20 along the rail causes mounting member 60 and thus the entire assembly 20 to rotate slowly on its vertical axis while traveling along this path. Driving wheel 88 merely increases the speed of rotation of assembly 20 at station 2 in order to insure uniform application of plastisol 75 to die wiper 42.

From station 2 assembly 20 is advanced by chain 16 to station 3 where a bar 94, formed of flexible elastic material, has a plurality of teeth 96 thereon projecting inwardly toward the assembly 20 positioned adjacent chain 16. Bar 94 is so positioned that teeth 96 engage neck 44 of die wiper 42 as the assembly is moved forwardly by the conveyor 14. This engagement causes rotation of the die wiper with respect to the bevel guide and the needle. This rotation of the die wiper insures full wetting of adjacent portions of the bevel guide and needle by the plastisol 75 in reservoir 46 and evens the plastisol about the annular extent of the reservoir.

After passing the end of station 3, that is, the end of bar 94, the entire assembly is removed manually from mounting member 60 and inverted to the position illustrated in FIG. 5 and replaced on mounting member 60 with the projecting boss 76 thereon inserted in the bore of needle handle 28. This is illustrated in phantom in FIG. 18. While in the illustrative embodiment of the present invention the step at station 4 is performed manually, it is contemplated that an automatic inverting mechanism may be utilized at station 4. Such an assembly may be any one of those presently used in various arts and which would be available to a skilled mechanic for inverting and replacing an article on a moving conveyor. Further, it is contemplated that other known devices may be utilized which invert an article in place. In such cases, conveyor chain 16 would be stopped when the assembly reaches station 4 in order for this operation to take place.

Once assembly 20 has been inverted at station 4 and moves toward station 5, the die wiper begins to move downwardly on shank 25 of needle 24 under the influence of gravity as illustrated in FIG. 6 and as a result a coating 85 of liquid plastisol 75 is wiped along the shank. This downward movement continues from station 4 through to station 8 and forms the catheter on needle shank 25.

Referring to FIG. 12 it is seen that in the initial position of the assembly, needle point 26 extends into reservoir 46 and is seated in the recess 56 of guide 48. The portions of tip 50 surrounding needle end 26 protect the tip from application of platisol 75 thereto. In addition, the beveled edge 51 of tip 50 defines the leading edge of the plastisol coating 85 on the shank of the needle so that the forward placement of the lip 53 of the catheter formed by the die wiper in coating the shank of the needle is precisely located. Bevel 51 of the guide and the depth of recess 56 are selected so that the lip 53 of the catheter is begun on the needle at a point thereon such that as the needle is inserted into the skin the lip of the catheter enters the skin after an initial slit has been cut by the needle and before the skin is stretched taut by the fullness insertion of the needle point. This is a substantial advantage over previously proposed catheters which had square cut catheter lips or shoulder placed completely behind the beveled tip of the needle. In such devices it often occured that the catheter was prevented from entering the skin because of engagement therewith by the catheter shoulder.

When the assembly is inverted, as mentioned above, die wiper 42 begins to move down the shank of the needle under the influence of gravity. FIG. 13 illustrates the die wiper position with respect to the bevel guide after a slight amount of movement thereof. Plastisol 75 is retained in reservoir 46 and as the die wiper moves downwardly, the plastisol tends to creep up into the neck 44 of the die wiper until the neck is completely filled as illustrated in FIG. 14.

It has been found that by laterally offsetting the neck portion 50 with respect to the central axis passing through portion 52 and recess 56 of bevel guide 48, so that a narrower wall portion 98 is provided adjacent the heel of the needle point 26 and a wider wall portion 100 is provided adjacent the toe thereof, the wall thickness of the coating 85 wiped on the needle adjacent the toe portion, as illustrated in FIG. 13, is thicker than the coating thickness adjacent the heel portion of the needle point. This is desirable since the toe portion of the completed catheter is unprotected as it enters the skin and additional strength is required at that point. An unexpected result is the die wiping of the plastisol on the needle to produce a tapered feather edge 102 at lip 53, after the bevel guide member 48 is removed, to facilitate insertion of the catheter. The plastic material 85', (FIG. 13) adjacent bevel guide edge 51 flows downwardly under the influence of gravity after the bevel guide is removed in order to form the feathered edge of the catheter 30. This again is a substantial improvement over prior catheters since the square cut and blunt edged catheters of previously proposed instruments often "curl back" on the needle when they engage the skin and thus cannot penetrate therethrough.

Another advantage of die wiping process of producing the catheter in accordance with the method of the present invention is that the catheter wall thus formed is tapered from lip 53 along a substantial length of the shank of the needle. This occurs because the neck of the die wiper is not completely filled with plastisol during the initial portions of the wiping process. As the die wiper traverses the shank the plastisol slowly fills neck 44, so that not all of the plastisol that moves into neck 44 is wiped on needle shank 25. As neck 44 fills, the thickness of the wiped-on coating increases and once the neck is filled the maximum catheter wall thickness is wiped on the needle. The thickness of the plastisol coating 85 of the needle at maximum wiping has been found to be equal to approximately ½ the distance between the shank and the interior surface of the neck of the die wiper.

In the preferred embodiment of the present invention, neck 44 is dimensioned so that the first ⅓ of the completed catheter has the tapered wall configuration. By lengthening the neck, the length of the taper in the catheter produced by the method of the present invention may be increased, since the die wiper must fall further along shank 25 before being filled. This taper of the catheter is advantageous since the initial portion of the catheter and needle represent the "feel" portion, that is, it is this portion of the needle and catheter assembly which is first inserted in the vein. During the insertion procedure, the physician can feel the difference in "drag" on the needle and catheter when the needle enters the vein. By having the tapered streamlined catheter, less drag is produced on the assembly so that it is easier for the physician to feel the difference in drag which occurs when the needle enters the vein.

Another improved result of the die wiping method of the present invention is the uniform wall of the resulting catheter.

From station 4, the assembly is moved in its inverted position to station 5. At this point the die wiper has dropped a very small distance and the major portion of the shank of the needle remains exposed. An impulse pump 104 is located at station 5 and has a beveled nozzle 106 which is positioned to engage the shank of the needle. The pump 104 delivers a plastisol having a radio opaque material, such as a fine tantalum powder suspended therein, through nozzle 106 and onto shank 25 of the needle (See FIGS. 1 and 6). The powder is in a matrix of substantially the same plastisol as the plastisol supplied to reservoir 46 and becomes incorporated in the coating of the catheter as the die wiper and plastisol move past the point of application thereof. Nozzle 106 is provided with a slotted aperture on its beveled face 108 which aperture is positioned an an angle of approximately 45° to the vertical so that as needle shank 25 is simultaneously rotated by engagement of member 60 with base 73 with a wheel 90' (driven by an electric motor or the like, not shown) and moved past the angularly positioned aperture, a helical stripe 95 of the radio opaque material is applied to the needle shank.

While the application of this material may be omitted in the method of the present invention, the provision thereof in the catheter is an optional safety feature which is useful in the event that the end of the catheter should break and pass into the circulation system of the body. In such a case, the location of the catheter could then be rapidly determined by X-ray procedures which would detect helical stripe 95 so that the location of the catheter could be accurately determined and surgically removed.

A guide system 110 is provided at station 5 (see FIG. 19) for holding shank 25 against face 108 of pump nozzle 106. This system includes a generally cylindrical member 116 having a lower cam surface 118. Cylindrical member 116 is fixed on a shaft 120 mounted in plate 12. A cylindrical sleeve 122 is rotatably mounted on shaft 120 and is secured to and thus rotated with sprocket 19. The upper portion of sleeve 122 includes a hub member 124 which supports a plurality of flexible guide fingers 126 having notches 128 in their ends. As sleeve 122 and hub 124 are rotated with sprocket 19, the notched ends 128 of the fingers 126 are sequentially moved into engagement with the shank of individual needles moving through station 5. At the position immediately opposite nozzle 106 cam surface 118 is at its highest point with respect to base 12 so that the finger 126 thereat is at a substantially horizontal position and holds shank 25 of the needle with which it is engaged against the elongated aperture of pump nozzle 106. As the needle moves out of station 5, the finger 126 moves with it, since it is rotating at the same speed as chain 16 and sprocket 19. However, the finger is engaged by cam surface 118 and is progressively bent downwardly and away from shank 25, until, at a position approximately 120° away from station 5, the finger is completely disengaged from the needle. Cam surface 118 holds the finger 126 in this lowered position as rotation thereof continues. However, as finger 126 contemplated that the needle be initially dipped in or coated with an inert silicon material before insertion of the assembly at station 1.

It is thus seen that the present invention provides an improved method and apparatus for making a catheter directly on the needle with which it is used to insert the catheter in a body cavity. It will also be observed that the present invention provides an improved catheter and needle unit which is of relatively simple and compact construction adapted for economical construction and one which is reliable in operation for inserting the end of a plastic catheter in a body cavity.

Although illustrative embodiments of the present invention have been described herein with reference to the accompanying drawings, it is to be understood that the invention is not limited to that precise embodiment and that various changes and modifications may be effected therein by one skilled in the art without departing from the scope or spirit of this invention. For example, the method of the present invention may be used to make plastic tubes for other uses than as catheters. Therefore, without limitation in this respect the invention is defined by the following claims.

What is claimed is:

1. The method of making a plastic catheter with the aid of a mandrel having an outside diameter corresponding to the diameter of the lumen of the catheter to be formed and a die wiper having at one end an orifice of somewhat larger diameter than the outside diameter of said mandrel and further having a reservoir in open communication with said orifice, said method comprising the steps of, placing said die wiper about a first end of said mandrel with the said orifice thereof facing in the same direction as said first end of said mandrel, applying a mass of an at least semi-viscous liquid plastic material on said mandrel at least adjacent said reservoir of said die wiper on the side thereof opposite said mandrels' first end, positioning said mandrel substantially vertically, structurally supporting only one of said die wiper or said mandrel and relatively moving said die wiper from said first end of the mandrel to the opposite end thereof in a manner such that the mandrel passes freely through said die wiper and the latter engages the mass of liquid plastic material previously applied to said mandrel and thereby wipes a coating of said plastic material onto the exterior of said mandrel, and then curing said liquid plastic material on said mandrel thereby forming a flexible catheter thereon.

2. The method of making a plastic catheter with the aid of a mandrel having an outside diameter corresponding to the diameter of the lumen of the catheter to be formed and a die wiper having an orifice of larger diameter than the outside diameter of said mandrel, said method comprising the steps of, placing said mandrel in an upright position with the orifice of the die wiper around its lower end, applying an at least semi-viscous liquid plastisol on said die wiper on the side thereof opposite said lower end, inverting the assembly of mandrel, die wiper and plastisol so that the die wiper falls by gravity and wipes a coating of plastisol between the exterior of said mandrel and the interior of said die orifice, and then heating the assembly to cure said liquid plastisol on said mandrel and form a flexible catheter thereon.

3. The method of making a combined needle and catheter of the type in which the needle is used to lead the end of the catheter thereon into a body cavity and, after insertion, is withdrawn through said catheter leaving the end of the catheter in the body cavity, said method, with the aid of a die wiper having an orifice of larger diameter than the outside diameter of said needle, comprising the steps of, placing said needle in an upright position with its pointed end downward and located in the orifice of the die wiper, applying a measured quantity of an at least semi-viscous fluid plastic material on said die wiper on the side thereof opposite said pointed end, inverting the assembly of said needle, die wiper and fluid plastic so that the die wiper falls by gravity and wipes a coating of the fluid plastic along the shank of said needle, and then heating the assembly to solidify the fluid plastic on said needle and form a removable flexible catheter thereon.

4. The method of claim 3 including the step of applying an inert radio opaque material to a predetermined portion of said needle prior to passage of said die wiper and plastic thereover.

5. The method of claim 3 including the step of applying a bead of liquid plastic material to a predetermined portion of said catheter, after said heating step, and then heating said bead to solidify the liquid plastic material and form a safety stop member on said catheter.

6. The method of claim 3 including the step of enclosing the top and a predetermined portion of said needle during said step of applying plastic to said die wiper and at least during the initial portion of wiping by said die wiper whereby said tip is left uncoated by plastic and said needle is coated from a predetermined point thereon.

7. The method of claim 3 including the step of surrounding the shank of said needle with a catheter reinforcing member prior to wiping of the needle by said die wiper.

8. The method fo making a combined needle and catheter of the type wherein a needle having a handle assembly is used to lead the end of a catheter thereon into a body cavity and, after insertion, is withdrawn through said catheter leaving the end of the catheter in the body cavity, said method comprising the steps of, inserting said needle through a preformed fitting member, frictionally engaging the interior of said catheter fitting member with said needle handle, inserting said needle through the central orifice of a die wiper having a reservoir portion opening towards said catheter fitting member, inserting the free end of said needle in a guide member, placing the assembly of needle, catheter hub, die wiper and guide member in an upright position at a first station with said guide member at the lower end of the assembly and the upper portion of the guide member surrounded by said die wiper, applying a measured quantity of an at least semi-viscous fluid plastisol of a plastic resin in the reservoir of said die wiper about said needle and the upper portion of said guide, rotating said assembly about its central vertical axis to fully distribute said plastisol in said reservoir and fully wet said needle, inverting said assembly so that said die wiper falls by gravity and wipes a substantially circumferentially uniform wall of the fluid plastisol along the entire shank of the needle above said catheter fitting member, then heating the assembly to solidify the fluid plastisol on said needle to form a removable flexible catheter thereon.

9. The method of claim 8 including the step of surrounding the shank of said needle above said catheter hub member with a catheter reinforcing member, prior again approaches station 5, cam surface 118 rises so that finger 126 may engage another needle.

As assembly 20 moves from station 5 to station 6, die wiper 42 continuously moves downwardly along the shank 25 of the needle 24 under the influence of gravity. At station 6, the die wiper has moved down on shank 25 a sufficient distance so that neck 44 thereof is free of bevel guide 48. At this point, bevel guide 48 is manually removed and discarded. However, it is contemplated that the removal operation can be automated by appropriate mechanical equipment. In any case, the removal of the bevel guide from the needle must be done rapidly in order that the plastisol breaks cleanly and does not smear the end of the needle.

The assembly moves from station 6 through station 7 where a bar 130, of similar construction to bar 92, is positioned to rotate assembly 20 engagement with the assembly support member 60. As a chain link 60 moves assembly 20 through station 7, and as die wiper 42 continues to move down shank 25 of the needle, the rotation of the assembly ensures lateral uniformity of temperature and position effects and concentricity of the catheter wall.

The length of station 7 is such that when the assembly passes the end of the station, the die wiper has wiped the entire length of shank 25 and its conical section 46 is seated on the upper portion of the catheter fitting 32 with neck 44 extending upwardly therefrom. At this point, station 8, die wiper 42 is engaged by cam members 132 positioned at opposite sides thereof, as illustrated in phantom lines in FIG. 9 to firmly seat the die wiper on the outer conical surface of the fitting 32 between the neck 44 and socket 36, (see FIG. 16). The relatively wet plastisol engaging the plastic fitting 32 is substantially the same material as plastic fitting 32, but in different form, and when subsequently heated the two plastic bodies are welded into a unified integral mass.

The liquid plastisol 85 on shank 25 has a slight tendency to flow downwardly of its own accord under the influence of gravity and thus a slight fillet 136 (see FIG. 9) also is formed at the point of juncture of the neck 44 of die wiper 42 with the plastisol on the shank 25. This fillet is advantageous in that it strengthens the point of juncture between the die wiper and the catheter and lessens the possibility of breakage of the catheter at this point. Further, the point of juncture of the catheter with the fitting is reinforced by the die wiper itself so that the disadvantage of previously proposed catheters, which often broke from the fitting at the point of juncture therebetween, is substantially reduced.

After passing through station 8 under cams 132, the assembly is moved through an infrared heater 138 at station 9 wherein the plastisol is cured and solidified to produce the completed flexible catheter 135 on the needle. In the preferred embodiment of the present invention the infrared heater heats the assembly for a minute and a quarter to approximately 370° F. The conveyor 16 continuously moves the assembly through the heater without stopping so that the other processes of the invention may continuously take place on other assemblies. It is noted that fitting 32 and formed tube are formed of the same plastic material and thus the heat curing of the plastisol also cures the welded joint between the tube and fitting.

From station 9 the entire assembly with the cured catheter 135 thereon passes through station 10 where impulse pump 140 is located. Pump 140 has a nozzle 142 and supplies a small bead 145 of liquid plastisol to the surface of catheter 135 at a location slightly spaced from the point of juncture of catheter 135 with the neck 44 of die wiper 42 (FIG. 10). Bead 145 is provided to limit the extent of insertion of the completed assembly through the skin into a body cavity, and also provides an additional safety feature in the unlikely event that the catheter should break at a point rearwardly of the bead since the engagement of the bead with the skin surface would prevent the catheter from entering the body.

A drive wheel 144, driven by a motor (not shown), also is located at station 10 and engages part 28 of assembly 20 to rotate the entire assembly 20. Impulse pump 140 is energized by a microswitch (not shown) which is engaged by part 28 as it passes into station 10. The rotation of assembly 20 by wheel 144 insures that a completely annular bead 145 is formed on the surface of the catheter.

From station 10 conveyor 16 moves the assembly through infrared heater 145 (station 11) which cures and solidifies only the liquid plastisol bead 145. After passing through station 11 the catheter and needle combination 150 is completed and the assembly is manually removed from the apparatus at station 12. The mounting member 60 on which the assembly is transported through the apparatus is then moved from station 12 through to station 1 and another assembly 20 is placed on the chain for production of another combined needle and catheter assembly.

Referring to FIG. 16 of the drawing, a completed needle and catheter assembly 150 is illustrated. As seen therein, the leading ⅓ of the catheter has a tapered wall thickness and a substantially constant wall thickness over the remainder of the shank. Plastisol material forming the catheter provides a layer between fitting 32 and die wiper 42 which is welded to the fitting and forms an integral bond therebetween. As mentioned above, fitting 32 is formed of the same plattic material as the liquid plastisol so that an integral bond is formed therebetween. Further, die wiper 42 serves as a reinforcement for the point of juncture between catheter and hub 32 and fillet 136 further reinforces the catheter at this point.

In another embodiment of the present invention, the assembly 20 utilized to form the catheter and needle combination may be provided with a reinforcing member about the shank of the needle. Such a reinforcing member may, as illustrated in FIG. 17, be a flexible coil spring 160. The shank of the needle is merely inserted in the spring prior to installation of the assembly at station 1 and the entire manufacturing process is completed as before. In this case, however, the coating of liquid plastisol is applied over the combination of needle, shank and spring and the spring is embedded in the coating during the curing process. This spring serves to reinforce the entire shank of the catheter after removal of the needle and further eliminates the possibility of breakage of the catheter when inserted in the body. While a coil spring has been illustrated in the drawings for use in the preferred embodiment, it is noted that other reinforcing materials may be used, such as for example, a plastic wire or mesh cylinder.

When the completed assembly is utilized to insert the catheter in the vein of a patient, needle 24 readily slides out of the catheter since no bonding takes place between the plastisol and the needle shank. However, to assist removal of the needle from the catheter it is to inverting said assembly and wiping of the needle by said die wiper.

10. The method of claim 8 including the step of forming a fillet at the juncture of the coating and the die wiper when said die wiper reaches said catheter hub assembly.

11. The method of claim 8 including the step of rotating said assembly during said application of radio opaque material to said needle to form a helical stripe of said material on said needle.

12. The method of claim 8 including the step of rotating said assembly during application of said bead to said catheter so that said bead comprises an annular ring on the catheter.

13. The method of making a plastic tubular article with the aid of a mandrel having an outside diameter corresponding to the diameter of the lumen of the tubular article to be formed and a die wiper having at one end an orifice of a slightly larger diameter than the outside diameter of said mandrel and of said tubular article to be formed and further having an enlarged reservoir in open communication with said orifice, said method comprising the steps of, placing said die wiper concentric to and adjacent one end of said mandrel and with said orifice facing in the same direction as said one end of said mandrel, charging an at least semi-viscous liquid plastic material into the reservoir of said die wiper and onto said mandrel thereat, causing relative falling movement by means of gravity of said die wiper along said mandrel with the latter in a substantially vertical orientation so that a substantially circumferentially uniform coating of said plastic material is drawn from said die wiper through said orifice onto the exterior of said mandrel passing therethrough, then treating the assembly to cure said coating of liquid plastic material on said mandrel and form said tubular article thereon.

14. The method as claimed in claim 1 wherein at least a portion of said catheter is formed with a taper by using a die wiper having an orifice formed with an elongated neck and starting the wiping along the mandrel without any liquid plastic material in the effective interior portion of said neck.

15. The method according to claim 1 including the step of rotating said die wiper and mandrel during their relative longitudinal movement to promote even distribution and wetting by said plastic material and circumferential uniformity in the resulting coating.

16. The method according to claim 6 including the step of applying a greater amount of plastic material near the toe of the point of said needle and a relatively lesser amount near the heel thereof and thereafter feathering the coated material at said point prior to curing.

17. The method according to claim 8 further comprising incorporating a radio opaque material in at least a predetermined portion of said plastisol used to form said catheter.

18. The method according to claim 17 further comprising applying a bead of liquid plastisol to a predetermined portion of the formed catheter and then heating said bead to solidify the liquid plastisol and form a safety stop member on said catheter.

19. The method of making a combined needle and catheter of the type in which the needle is used to lead the end of the catheter thereon into a body cavity and, after insertion, is withdrawn through said catheter leaving the end of the catheter in the body cavity, wherein said needle includes a distal end and a proximal end, said method, with the aid of a die wiper having at one end an orifice of somewhat larger diameter than the outside diameter of said needle, comprising the steps of; positioning said die wiper over said needle adjacent said distal end thereof with said orifice oriented away from said proximal end, applying an at least semi-viscous liquid plastic material to said needle on the side of said positioned die wiper which faces said proximal end of said needle in a measured quantity sufficient to form a catheter thereon, moving said die wiper with respect to said needle from said distal end thereof toward said proximal end thereof with only one of said needle and said die wiper being structurally supported so that said die wiper freely wipes a coating of said plastic material onto said needle to form a catheter thereon, and curing said plastic material on said needle.

20. The method according to claim 19 wherein the amount of the measured quantity of plastic is sufficient to form a catheter with slight excess.

21. The method according to claim 20 wherein said die wiper comes to rest positioned adjacent the proximal end of the needle and upon curing of the catheter becomes, together with said excess, a part of a reinforced hub portion of the catheter.

22. The method according to claim 19 wherein said catheter is formed by said die wiper freely wiping along said needle in the vertical orientation.

23. The method according to claim 19 wherein said die wiper is positioned at the lower-distal end of said mandrel and after the plastic material has been charged, the mandrel is inverted, causing the die wiper to fall by gravity down along said inverted mandrel toward its proximal end.

24. The method according to claim 19 including the step of rotating said needle relative to said die wiper after said plastic material applied to said needle has been engaged by said die wiper so as to more evenly distribute said plastic material about said needle.

25. The method according to claim 19 wherein said die wiper has an elongated neck portion in the form of a hollow tube defining said orifice at one end thereof and having flaired out from the other end thereof and enlarged reservoir such that initially only a portion of the plastic material drawn from said reservoir of said die wiper by said mandrel actually coats the exterior of said mandrel and the remainder thereof in increasing amounts progressively fills said neck portion with such plastic material thereby giving a tapered coating of an increasing thickness of plastic material along the exterior length of said mandrel until said neck portion is filled.

\* \* \* \* \*

UNITED STATES PATENT AND TRADEMARK OFFICE
CERTIFICATE OF CORRECTION

PATENT NO. : 3,943,225
DATED : March 9, 1976
INVENTOR(S) : Wilbur R. Koehn

It is certified that error appears in the above-identified patent and that said Letters Patent are hereby corrected as shown below:

Claim 8, line 37, "fo" should be --of--;

Claim 25, line 51 "and" in the second occurrence should be --an--.

Signed and Sealed this eighteenth Day of May 1976

[SEAL]

Attest:

RUTH C. MASON
Attesting Officer

C. MARSHALL DANN
Commissioner of Patents and Trademarks